United States Patent
Wei et al.

(10) Patent No.: US 11,788,981 B2
(45) Date of Patent: *Oct. 17, 2023

(54) SENSOR FOR DETECTING GAS ANALYTE

(71) Applicant: CARRIER CORPORATION, Palm Beach Gardens, FL (US)

(72) Inventors: Alexander Wei, West Lafayette, IN (US); Lia Antoaneta Stanciu, West Lafayette, IN (US); Winston Yen-Yu Chen, West Lafayette, IN (US); Aiganym Yermembetova, West Lafayette, IN (US); Benjamin M. Washer, Lafayette, IN (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 644 days.

This patent is subject to a terminal disclaimer.

(21) Appl. No.: 16/811,687

(22) Filed: Mar. 6, 2020

(65) Prior Publication Data

US 2020/0292481 A1 Sep. 17, 2020

Related U.S. Application Data

(60) Provisional application No. 62/816,677, filed on Mar. 11, 2019.

(51) Int. Cl.
| | | |
|---|---|---|
| *G01N 27/12* | (2006.01) | |
| *G01N 33/00* | (2006.01) | |
| *C07F 1/08* | (2006.01) | |
| *C01G 39/06* | (2006.01) | |
| *C01G 41/00* | (2006.01) | |
| *G01N 27/416* | (2006.01) | |
| *B82Y 30/00* | (2011.01) | |

(52) U.S. Cl.
CPC .......... *G01N 27/127* (2013.01); *C01G 39/06* (2013.01); *C01G 41/00* (2013.01); *C07F 1/08* (2013.01); *G01N 27/4162* (2013.01); *G01N 33/0047* (2013.01); *B82Y 30/00* (2013.01); *C01P 2004/16* (2013.01); *C01P 2004/64* (2013.01)

(58) Field of Classification Search
None
See application file for complete search history.

(56) References Cited

U.S. PATENT DOCUMENTS

| | | |
|---|---|---|
| 2013/0273665 A1 | 10/2013 | Swager et al. |
| 2015/0247832 A1 | 9/2015 | Swager et al. |
| 2020/0291044 A1 | 9/2020 | Wei et al. |
| 2020/0291053 A1 | 9/2020 | Wei et al. |

OTHER PUBLICATIONS

Chen et al., "Selective Detection of Ethylene by MoS2—Carbon Nanotube Networks Coated with Cu(l)—Pincer Complexes", ACS Sensors,2020, No. 5, pp. 1699-1706.
Esser et al., "Selective Detection of Ethylene Gas Using Carbon Nanotube-based Devices: Utility in Determination of Fruit Ripeness", Angew. Chem. Int. Ed. 2012, No. 51, pp. 5752-5756.
European Search Report for European Application No. 20162145.5; Application Filing Date: Mar. 10, 2020; dated Aug. 5, 2020, 7 pages.
Fu et al., "Ultrasensitive Ethene Detector Based on Graphene-Copper(l) Hybrid Material", Nano Lett. 2017, No. 17, pp. 7980-7988.
Ojo et al., 2001, caplus an 2001:153627.
Ping et al., "Recent Advances in Sensing Applications of Two-Dimensional Transition Metal Dichalcogenide Nanosheets and Their Composites", Advanced Functional Materials, 2017, No. 27, 18 pages.
Reglinski et al., 1999, caplus an 1999:418573.
Kimblin et al: "Bis(mercaptoimidazolyl)(pyrazolyl)hydroborato Complexes of Zinc, Cadmium, and Cobalt: Structural Evidence for the Enhanced Tendency of Zinc in Biological Systems to Adopt Tetrahedral M[S4] Coordination" Inorganic Chemistry, vol. 39, No. 19, Aug. 22, 2000, pp. 4240-4243.
Maffett et al.; "Nickel Nitrosyl Complexes in a Sulfur-Rich Environment: The First Poly(mercaptoimidazolyl)borate Derivative"; Elsevier; ScienceDirect; Polyhedron 26; pp. 4758-4764; Jun. 23, 2007.
Patel et al.; "Gold(l) Tris(mercaptoimidazolyl)borage Chmistry: Synthesis and Molecular Structure of the First Trinuclear TmR Complex of a Transition Metal"; Elsevier; ScienceDirect: Inorganic Chemistry Communications 9; pp. 748-750; Apr. 27, 2006.
White et al.; "Synthesis and Structural Characterization of 2-mercapto-1-tert-butylimidzole and its Group 12 Metal Derivatives (HmimtBu2MBr2 (M=Zn, Cd, Hg)"; Journal of Chemical Crystallography, vol. 33, Nos. 5/6, 9 Pages, Jun. 2003.

*Primary Examiner* — Alexandre F Ferre
(74) *Attorney, Agent, or Firm* — CANTOR COLBURN LLP

(57) ABSTRACT

A sensor and a method of using the sensor are disclosed. The sensor includes a conductive region in electrical communication with two electrodes, the conductive region including metallic nanowires, nanosized particles of a dichalcogenide, and a mercaptoimidazolyl metal-ligand complex. The sensor can be used to detect volatile compounds that have a double or triple bond.

18 Claims, No Drawings

SENSOR FOR DETECTING GAS ANALYTE

CROSS REFERENCE TO RELATED APPLICATIONS

This application claims the benefit of U.S. Provisional Patent Application No. 62/816,677 filed on Mar. 11, 2019 which is incorporated by reference herein in its entirety.

BACKGROUND

Exemplary embodiments pertain to the art of sensor compositions based on metal complexes.

Volatile compounds with a double or triple bond form an important group of compounds for detection. In particular, volatile alkenes, such as ethylene, are analytes of considerable importance. In particular, the detection of ethylene is important to industries related to produce and agriculture. Due to its small size and limited chemical functionality, however, ethylene is a challenging chemical analyte to detect. More efficient and sensitive methods of detection than those currently available are desired.

BRIEF DESCRIPTION

Disclosed is a sensor including a conductive region in electrical communication with two electrodes, the conductive region including metallic nanowires, nanosized particles of a metal dichalcogenide, and a mercaptoimidazolyl metal-ligand complex.

In addition to one or more of the features described above, or as an alternative to any of the foregoing embodiments, the nanosized particles of a metal dichalcogenide include $MoS_2$, $WS_2$, $MoSe_2$, $WSe_2$, $MoTe_2$, $WTe_2$, and combinations thereof.

In addition to one or more of the features described above, or as an alternative to any of the foregoing embodiments, the mercaptoimidazolyl metal-ligand complex includes more than one mercaptoimidazolyl groups.

In addition to one or more of the features described above, or as an alternative to any of the foregoing embodiments, the mercaptoimidazolyl metal-ligand complex includes three mercaptoimidazolyl groups.

In addition to one or more of the features described above, or as an alternative to any of the foregoing embodiments, the mercaptoimidazolyl metal-ligand complex includes a pyrazolyl or indolyl group in addition to the mercaptoimidazolyl group(s).

In addition to one or more of the features described above, or as an alternative to any of the foregoing embodiments, the mercaptoimidazolyl metal-ligand complex includes Cu(I), Ag(I), or Au(I).

In addition to one or more of the features described above, or as an alternative to any of the foregoing embodiments, the mercaptoimidazolyl metal-ligand complex is a complex of formula (II):

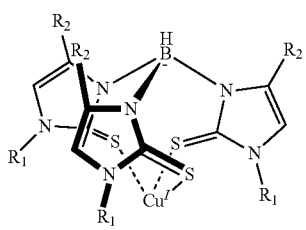

(II)

where each instance of $R_1$ and $R_2$ can be hydrogen or a group containing one or more carbon atoms.

Also disclosed is a method of sensing a volatile compound having a double or triple bond including exposing a sensor to a sample, the sensor including a conductive region in electrical communication with two electrodes, the conductive region including metallic nanowires, nanosized particles of a metal dichalcogenide, and a mercaptoimidazolyl metal-ligand complex, and measuring an electrical property at the electrodes.

In addition to one or more of the features described above, or as an alternative to any of the foregoing embodiments, the electrical property is conductivity.

In addition to one or more of the features described above, or as an alternative to any of the foregoing embodiments, the electrical property is resistivity.

In addition to one or more of the features described above, or as an alternative to any of the foregoing embodiments, the method further includes comparing the electrical property value obtained by measuring to a calibration curve to determine the quantity of a volatile compound having a double or triple bond present in the sample.

In addition to one or more of the features described above, or as an alternative to any of the foregoing embodiments, the volatile compound having a double or triple bond is ethylene.

In addition to one or more of the features described above, or as an alternative to any of the foregoing embodiments, the nanosized particles of a metal dichalcogenide include $MoS_2$, $WS_2$, $MoSe_2$, $WSe_2$, $MoTe_2$, $WTe_2$, and combinations thereof.

In addition to one or more of the features described above, or as an alternative to any of the foregoing embodiments, the mercaptoimidazolyl metal-ligand complex includes more than one mercaptoimidazolyl group.

In addition to one or more of the features described above, or as an alternative to any of the foregoing embodiments, the mercaptoimidazolyl metal-ligand complex includes three mercaptoimidazolyl group.

In addition to one or more of the features described above, or as an alternative to any of the foregoing embodiments, the mercaptoimidazolyl metal-ligand complex includes a pyrazolyl or indolyl group in addition to the mercaptoimidazolyl group(s).

In addition to one or more of the features described above, or as an alternative to any of the foregoing embodiments, the mercaptoimidazolyl metal-ligand complex includes Cu(I), Ag(I), or Au(I).

In addition to one or more of the features described above, or as an alternative to any of the foregoing embodiments, the mercaptoimidazolyl metal-ligand complex is a complex of formula (II):

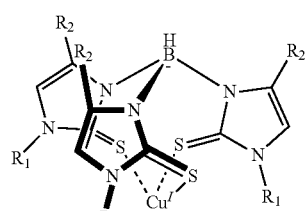

(II)

where each instance of $R_1$ and $R_2$ can be hydrogen, or a group containing one or more carbon atoms.

In another aspect, a method of preparing a sensor includes forming a conductive region including metallic nanowires, a nanosized particles of a metal dichalcogenide, and a mercaptoimidazolyl metal-ligand complex, and placing the conductive region in electrical communication with two electrodes.

DETAILED DESCRIPTION

A detailed description of one or more embodiments of the disclosed apparatus and method are presented herein by way of exemplification and not limitation.

Volatile compounds with a double or triple bond is a group of important compounds for detecting and monitoring. The term volatile, as used herein, refers to compounds that are in the gas phase at standard temperature and pressure. Exemplary compounds include $NO_2$, $CO_2$, CO and alkenes such as $C_2H_4$ (ethylene). As the hormone responsible for initiating the ripening of fruit as well as other processes in plant development, ethylene is an analyte of considerable importance to industries related to produce and agriculture. Due to its small size and limited chemical functionality, ethylene and other volatile alkenes are challenging chemicals to detect. Disclosed herein is a sensor and a method that is capable of detecting volatile compounds with double bonds such as ethylene and other volatile alkenes at levels down to 100 parts per billion (ppb).

The sensor includes a conductive region in electrical communication with at least two electrodes. The conductive region includes metallic nanowires, nanosized particles of metal dichalcogenide, and a mercaptoimidazolyl metal-ligand complex.

Metallic nanowires are known materials and are commercially available. Nanowires may have a width of 10 nanometers to 1 micrometer and can have a length of 10 micrometers to 1 or more millimeters. Nanowires may have a length to width ratio greater than 1000. The nanowires can comprise one or more elements from Groups 1 12 as well as Al, Ga, In, Sn, Tl, Pb and Bi. In some embodiments the metallic nanowires comprise one or more of Ni, Cu, Au, Pt, or Ag. Methods for nanowire fabrication are described in U.S. Pat. No. 6,843,902.

Metal dichalcogenides include transition metal dichalcogenides which are compounds formed from a Group 6B metal and a chalcogenide (S, Se, and Te). Exemplary metal dichalcogenides include $MoS_2$, $WS_2$, $MoSe_2$, $WSe_2$, $MoTe_2$, $WTe_2$, and combinations thereof. The metal dichalcogenide is in the form of nanosized particles. "Nanosized" as it applies to the metal dichalcogenides refers to the fact that the material has a thickness of less than or equal to 100 nanometers. The metal dichalcogenides are typically available in a flake form with a thickness of 100 nanometers of less although other physical forms are not excluded with the caveat that the physical form has a linear dimension that is less than or equal to 100 nanometers.

The mercaptoimidazolyl metal-ligand complex is a multidentate coordination complex comprising one or more mercaptoimidazolyl groups. The arms of the multidentate ligand (groups on the boron atom) can be the same (homoleptic) or different (heteroleptic). For example, one arm can comprise a mercaptoimidazolyl group and a second arm can comprise a pyrazolyl or indolyl group. It is also contemplated that a multidentate ligand may comprise more than one mercaptoimidazolyl group or a combination of mercaptoimidazolyl group(s) and pyrazolyl group(s) or indolyl groups or both. The mercaptoimidazolyl metal-ligand complex may have formula (I)

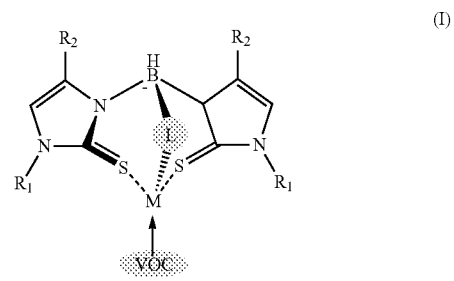

(I)

where each instance of $R_1$ and $R_2$ can be hydrogen or a group having one or more carbons. In some embodiments, each instance of $R_1$ and $R_2$ can be hydrogen or an alkyl group having 1 to 5 carbons. L in formula (I) can be a pyrazolyl group, a mercaptoimidazolyl group, or an indolyl. When L is a mercaptoimidazolyl group the multidentate metal-ligand complex can be described as homoleptic. When L is a group other than a mercaptoimidazolyl group the metal ligand complex can be described as a heteroleptic. VOC in formula I is present to show a postulated interaction with the volatile compound having a π bond. Without being bound by theory it is believed that the π bond of the volatile compound coordinates with an empty coordination site on the metal-ligand complex. The coordination alters the electronic configuration of the complex and can impact the electrical properties of the combination of the metal-ligand complex, nanosized particles of a metal dichalcogenide and metallic nanowires. In the case of a metal complex having formula II shown below, the resistivity of the combination of metal-ligand complex, nanosized particles of a metal dichalcogenide and metallic nanowires increases when the metal complex is bound to ethylene.

A more specific example of a mercaptoimidazolyl metal complex is shown in formula (II).

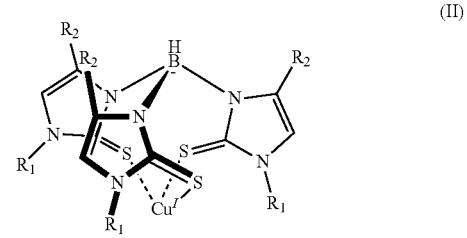

(II)

In formula (II) there are three mercaptoimidazolyl groups. $R_1$ and $R_2$ are defined as in formula (I).

The metal in the mercaptoimidazolyl metal complex may include Group 11 elements such as Cu(I), Ag(I), and Au(I).

The metallic nanowires and nanosized particles of a metal dichalcogenide are applied to a substrate. The substrate may be a flexible polymer film or other suitable material. Exemplary flexible polymer films include polyethylene terephthalate, polyethylene, polypropylene, polyamide, and polyvinyl chloride. The electrodes may be deposited on the substrate before the application of the metallic nanowires and nanosized particles of metal dichalcogenide. The metallic nanowires and metal dichalcogenide particles may be applied by spray deposition. These materials are either co-deposited or sequentially deposited. After the metallic nanowires and nanosized particles of metal dichalcogenide are applied to the substrate the mercaptoimidazolyl metal complex is deposited on top of the metallic nanowires and nanosized particles of metal dichalcogenide. The mercaptoimidazolyl metal complex may be applied by drop casting, dip coating, spray coating, or by electrospray. The layered material is then dried and is ready for use.

A method of sensing a volatile compound having a double or triple bond includes exposing a sensor as described above to a sample and measuring an electrical property of a two-electrode system. The electrical property can be conductivity or resistivity. The method can also include comparing the obtained electrical property value to a calibration curve to determine the quantity of the volatile compound present in the sample.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A sensor comprising a conductive region in electrical communication with two electrodes, the conductive region comprising metallic nanowires, nanosized particles of a metal dichalcogenide, and a mercaptoimidazolyl metal complex.

2. The sensor of claim 1, wherein the nanosized particles of a metal dichalcogenide comprise $MoS_2$, $WS_2$, $MoSe_2$, $WSe_2$, $MoTe_2$, $WTe_2$, and combinations thereof.

3. The sensor of claim 1, wherein the mercaptoimidazolyl metal complex comprises a homoleptic ligand with three mercaptoimidazolyl groups.

4. The sensor of claim 1, wherein the mercaptoimidazolyl metal complex comprises a heteroleptic ligand with a pyrazolyl or indolyl group in addition to a mercaptoimidazolyl group.

5. The sensor of claim 1, wherein the mercaptoimidazolyl metal complex comprises Cu(I), Ag(I), or Au(I).

6. The sensor of claim 1, wherein the mercaptoimidazolyl metal complex is a complex of formula (II):

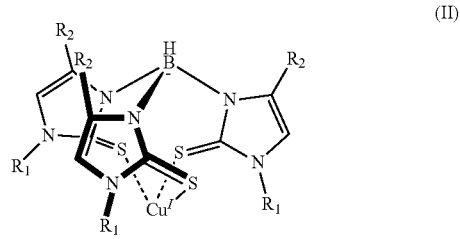

where each instance of $R_1$ and $R_2$ can be hydrogen or a group having one or more carbon atoms.

7. The sensor of claim 1, wherein the metallic nanowires comprise one or more of Ni, Cu, Au, Pt, or Ag.

8. A method of sensing a volatile compound having a double or triple bond comprising exposing the sensor of claim 1 to a sample, and measuring an electrical property at the electrodes.

9. The method of claim 8, wherein the electrical property is conductivity.

10. The method of claim 8, wherein the electrical property is resistivity.

11. The method of claim 8, further comprising comparing an electrical property value obtained by measuring to a calibration curve to determine the quantity of the volatile compound having a double or triple bond present in the sample.

12. The method of claim 11, wherein the volatile compound having a double or triple bond is ethylene.

13. The method of claim 8, wherein the nanosized particles of a metal dichalcogenide comprise $MoS_2$, $WS_2$, $MoSe_2$, $WSe_2$, $MoTe_2$, $WTe_2$, and combinations thereof.

14. The method of claim 8, wherein the mercaptoimidazolyl metal complex comprises three mercaptoimidazolyl groups.

15. The method of claim 8, wherein the mercaptoimidazolyl metal complex comprises a pyrazolyl or indolyl group in addition to the mercaptoimidazolyl groups.

16. The method of claim 8, wherein the mercaptoimidazolyl metal complex comprises Cu(I), Ag(I), or Au(I).

17. The method of claim 8, wherein the mercaptoimidazolyl metal complex is a complex of formula (II):

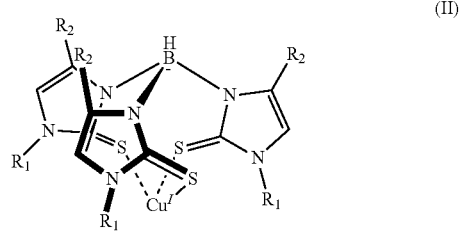

where each instance of $R_1$ and $R_2$ can be hydrogen or a group comprising one or more carbon atoms.

18. A method of preparing the sensor of claim 1, comprising
forming the conductive region including metallic nanowires, nanosized particles of the metal dichalcogenide, and the mercaptoimidazolyl metal complex, and
placing the conductive region in electrical communication with the two electrodes.

\* \* \* \* \*